United States Patent [19]

Andrean et al.

[11] Patent Number: 5,205,837
[45] Date of Patent: Apr. 27, 1993

[54] PRODUCT BASED ON INORGANIC OR ORGANIC LAMELLAR PARTICLES, CONTAINING A MELANOTIC PIGMENT, PROCESS FOR PREPARING IT AND ITS USE IN COSMETICS

[75] Inventors: Hervé Andrean, Paris; Alex Junino, Livry-Gargan, both of France

[73] Assignee: L'Oreal, Paris, France

[21] Appl. No.: 731,046

[22] Filed: Jul. 16, 1991

[30] Foreign Application Priority Data

Jul. 16, 1990 [FR] France .................. 90 09053

[51] Int. Cl.⁵ .............................................. A61K 7/13
[52] U.S. Cl. ........................................ 8/405; 8/406; 8/414; 8/416; 8/423; 424/70
[58] Field of Search ................. 8/405, 406, 414, 416, 8/423; 424/70; 132/38

[56] References Cited

FOREIGN PATENT DOCUMENTS 191292  8/1986  European Pat. Off. .
0220617 6/1987  European Pat. Off. .
2207153 1/1989  United Kingdom .

Primary Examiner—Paul Lieberman
Assistant Examiner—William S. Parks
Attorney, Agent, or Firm—Cushman, Darby & Cushman

[57] ABSTRACT

The invention relates to a product in powder form consisting of organic or inorganic particles having a lamellar structure, having a size of less than 50 microns and containing at least one synthetic melanotic pigment formed in situ by oxidation of an indole compound, and to its use for the protection of the human epidermis, in make-up products and for dyeing hair.

23 Claims, No Drawings

PRODUCT BASED ON INORGANIC OR ORGANIC LAMELLAR PARTICLES, CONTAINING A MELANOTIC PIGMENT, PROCESS FOR PREPARING IT AND ITS USE IN COSMETICS

The present invention relates to a product in the form of inorganic or organic lamellar particles, containing melanotic pigments, to a process for preparing it and to its use, in particular in the cosmetics field, for dyeing hair, make-up for body hair and/or the skin and the protection of the human epidermis against UV radiation.

The color of the hair, the skin and body hair of human origin originates in the main from the melanotic pigments secreted by melanocytes.

These pigments, which are of natural origin, comprise in particular black or brown pigments which are termed eumelanins.

Their natural biosynthesis takes place in several steps by polymerization of oxidation products of an amino acid, tyrosine, and one of these oxidation products is 5,6-dihydroxyindole, which in its turn polymerizes to eumelanin.

In prior patent applications and patents, there have been described various processes enabling human hair or the skin to be dyed using 5,6-dihydroxyindole or its derivatives, employing various oxidation systems. The colorings thus formed are fixed in or penetrate into the keratinous substrate.

On some occasions it is desired to be able to confer to the hair a coloring which is able to be removed rapidly if necessary.

Moreover, in make-up compositions for the skin, body hair, eyelashes or eyebrows, pigments based on metal compounds such as, for example, black and brown iron oxides, are used. However, these pigments are not completely innocuous and because of this pigments able to present fewer problems when used cosmetically are being sought.

The applicants just discovered that it is possible to prepare, in vitro, a product in the form of a powder formed of inorganic or organic lamellar particles, containing one or more melanotic pigments.

The applicants have discovered that the use of lamellar particles is particularly advantageous to the extent that these particles, once introduced into a cosmetically acceptable medium, disperse well within the composition which spreads easily on the hair or the skin and has a significant covering power.

Moreover, it has been found that they have an ultraviolet radiation absorption coefficient which is particularly worthwhile compared with the products known to date.

Particles termed "lamellar particles" according to the invention are particles which are in the form of thin plates, which may be layered.

These thin plates are characterised by a thickness which is less than the largest dimension. Preferably, the ratio between the largest dimension and the thickness is between 2 and 100.

The term "melanotic pigment" is used to denote the pigment formed by oxidation of 5,6-dihydroxyindole, optionally in combination with 5,6-dihydroxyindole-2-carboxylic acid.

By analogy and simplification, the pigment formed by oxidation of the various compounds of formula (I) defined below will be termed "melanotic pigment".

The subject of the present invention is therefore a powder consisting of inorganic or organic particles of lamellar structure, containing melanotic pigments.

Another subject of the invention comprises the preparation of such a powder.

A further subject of the invention is the cosmetic application of such powders, in particular in make-up products for the skin and body hair (eyelashes and eyebrows), protection of the human epidermis against UV radiation and hair dyeing.

Further subjects of the invention will become apparent on reading the description and the examples which follow.

The product according to the invention is essentially characterized in that it is in the form of a powder consisting of inorganic or organic particles of lamellar structure, the largest dimension of which is less than 50 microns, and containing, in or on the lamellar structure, a synthetic melanotic pigment formed in situ.

The melanotic pigment results from the oxidation of at least one indole dye, corresponding to the formula:

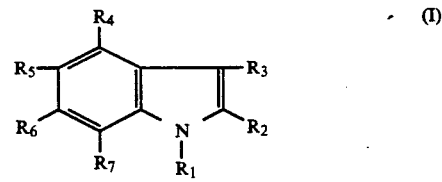

in which:

$R_1$ and $R_3$ denote, independently of one another, a hydrogen atom or a $C_1-C_4$ alkyl group;

$R_2$ represents a hydrogen atom, a $C_1-C_4$ alkyl group, a carboxyl group or a $(C_1-C_4)$alkoxycarbonyl group;

$R_4$ and $R_7$ denote, independently of one another, a hydrogen atom, a hydroxyl group or a $C_1-C_4$ alkyl, amino, $(C_1-C_4)$ alkoxy, $(C_2-C_4)$ acyloxy or $(C_2-C_4)$ acylamino group;

$R_5$ denotes hydrogen or a hydroxyl, $(C_1-C_4)$ alkoxy, $(C_1-C_4)$ alkyl, halogen, amino, $(C_2-C_{14})$ acyloxy, $(C_2-C_4)$ acylamino or trimethylsilyloxy group;

$R_6$ denotes hydrogen or a hydroxyl, $(C_1-C_4)$ alkoxy, amino, $(C_2-C_4)$ acyloxy, $(C_2-C_4)$ acylamino, trimethylsilyloxy or hydroxy$(C_2-C_4)$alkylamino group;

it being possible for $R_3$ and $R_5$ to form, conjointly with the carbon atoms to which they are attached, a methylenedioxy ring, which may be substituted by a $C_1-C_4$ alkyl or $C_1-C_4$ alkoxy group or a carbonyldioxy ring; at least one of the groups $R_4$ to $R_7$ represents an OZ or NHR group and at most one of the groups $R_4$ to $R_7$ denotes NHR; and at most two of the groups $R_4$ to $R_7$ denote OZ, and in the case where Z denotes hydrogen these groups are in the 5- and 6-positions;

and at least one of the groups $R_4$ to $R_7$ represents hydrogen, and in the case where only one of these groups denotes hydrogen, only one group from $R_4$ to $R_7$ then denotes NHR or OZ and the other groups denote $C_1-C_4$ alkyls;

R in NHR denoting a hydrogen atom or a $C_2-C_4$ acyl or $C_2-C_4$ hydroxyalkyl group and Z in OZ denoting a hydrogen atom or a $C_2-C_{14}$ acyl, $C_1-C_4$ alkyl or trimethylsily group; and the corresponding salts.

The indole dyes of formula (I) are preferably chosen from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, and 5,6-dimethoxyindole.

5,6-Dihydroxyindole and 6-hydroxyindole are particularly preferred.

The particles of lamellar structure are chosen in particular from the following products: L-lauroyllysin, such as the product sold under the name AMIHOPE L.L. by AJINOMOTO; ceramic microparticles optionally covered with zirconium powder, such as the products sold under the names TORAYCERAM ZP 550 and ZP 4000 by TORAY; lamellar titanium dioxide, such as the products sold under the names LUXELEN SILK D and LUXELEN SS by SUMITOMO, lamellar talc, boron nitride, such as the products sold under the names boron-nitride SF or SHP by WACKER and KAWASAKI; lamellar mica, such as the product sold under the name MICA CONCORD 1000 by SCIAMA; bismuth oxychloride, such as the product sold under the name PEARL GLO by MALLINCKRODT; and red transparent iron oxide, such as the product sold under the name CAPPOXYT 4435 B by CAPPELLE.

The size of the particles of lamellar structure used in accordance with the invention is preferably less than 50 microns and in particular less than 25 microns. Their size is generally larger than 0.5 micron. It is in particular between 1 and 20 microns. These particles have a thickness of generally more than 0.01 micron. As indicated above, these lamellar particles may be in the form of a layered structure.

The product according to the invention is preferably prepared by a process consisting in mixing the indole compound of formula (I) and the particles of lamellar structure defined above, in a medium which is essentially a non-solvent for the lamellar particles, in air and at a temperature which is preferably ambient and can range up to 100° C.

The oxidation of the indole compound of formula (I) may take place in an aqueous or aqueous/solvent medium, in air, or in air in the presence of an alkaline agent and/or a metal oxidation catalyst.

A preferred metal oxidation catalyst is the cupric ion.

The oxidation may also take place by using hydrogen peroxide in the presence of an alkaline agent, such as, preferably, ammonia, or in the presence or an iodide ion, the iodide preferably being an alkali metal iodide, alkaline earth metal iodide or ammonium iodide.

The oxidation may also be carried out using periodic acid and its water-soluble salts and derivatives, permanganates and bichromates, such as sodium or potassium permanganates and bichromates, sodium hypochlorite, potassium ferricyanide, ammonium persulphate, silver oxide, lead oxide, ferric chloride, sodium nitrite, rare earth salts, in particular cerium salts, and organic oxidizing agents chosen from ortho- and parabenzoquinone, ortho- and para-benzoquinone monoimines or diimines, 1,2- and 1,4-naphthoquinones, and 1,2- and 1,4-naphthoquinone monoimines or diimines. The preferred periodic acid salt is sodium periodate.

It is possible to activate the oxidizing agents using a pH modifying agent.

For example, when using the iodide/hydrogen peroxide system, an alkaline medium is preferably employed, which permits the reaction to be activated.

The process particularly preferred consists in using an alkali metal iodide, alkaline earth metal iodide or ammonium iodide, and hydrogen peroxide at an acid or alkaline pH and in this case the medium is ammonia.

The reaction medium used to form the dye on and in the particles having a lamellar structure is a medium which is essentially a non-solvent for the particles having a lamellar structure which are under consideration. It preferably consists of water and may optionally consist of a mixture of water and solvent(s). The solvent is chosen such that it rapidly dissolves the indole compound of formula (I).

Amongst these solvents, the following may be mentioned by way of example: $C_1$–$C_4$ lower alcohols such as ethyl alcohol, propyl or isopropyl alcohol or tert-butyl alcohol, alkylene glycols, such as ethylene glycol or propylene glycol, alkylene glycol alkyl ethers, such as ethylene glycol monomethyl, monoethyl and monobutyl ethers, propylene glycol monomethyl ether and dipropylene glycol monomethyl ether, and methyl lactate.

When the medium consists of a water/solvent(s) mixture, the solvent(s) is (are) present in concentrations of between 0.5 and 90% by weight relative to the total weight of the composition, in particular between 2 and 50% by weight and preferably between 2 and 20% by weight.

The nature of the solvents is chosen, and their proportion is adjusted, depending on the solubility criteria for the indole derivatives of formula (I) and the insolubility criterion for the lamellar particles.

In the process for the preparation of the products in the form of particles according to the invention, the indole compound is preferably used in proportions by weight of between 0.1 and 10% and preferably between 0.5 and 5% by weight relative to the total weight of the reaction mixture, the lamellar filler representing 0.05 to 35% by weight of the reaction mixture, the remainder of the reaction mixture generally consisting of water or a water/solvent(s) mixture.

The oxidizing agents are used in amounts sufficient to form, by oxidation, the melanotic pigment.

When an iodide ion is used to form the melanotic pigment, the said pigment is preferably used in proportions of between 0.07 and 4% and in particular between 0.7 and 3%, maintaining an indole dye/$I^-$ ratio of between 0.6 and 6 and more particularly between 3 and 4.

The proportions are determined relative to the weight of the reaction mixture.

The powder in the form of organic or inorganic particles having a lamellar structure and containing the melanotic pigment as defined above may be added to conventional cosmetic carriers in a concentration of between 0.1 and 35% by weight and preferably between 0.5 and 20% by weight, relative to the total weight of the composition, in order to lead to cosmetic compositions which protect the human epidermis, make-up products, such as for the eyelashes, the eyebrows or the skin, such as eye shadow, rouge, liners, also termed "eye liners", mascaras for the eyelashes and the eyebrows or tinctorial compositions for hair. These cosmetic carriers are known per se.

The compositions may be, in particular, in the form of a lotion, thickened lotion, gel, cream, milk, powder or stick and if appropriate may be packaged in an aerosol and be in the form of a foam or spray.

When the compositions are used for making up the skin, the eyelashes and the eyebrows, they may, in particular, be in anhydrous or aqueous solid or pasty form, such as oil-in-water or water-in-oil emulsions, or suspensions. These compositions have the advantage of being stable and of having good safety characteristics.

When the compositions are used for the protection of the human epidermis against UV radiation, they are compositions known as "sun" compositions and may be in the form of suspensions or dispersions in solvents or fats, or in the form of emulsions, such as creams and milks, ointments, gels, solid sticks or aerosol foams.

In all cases, when they are used in the form of emulsions, they may also contain surface-active agents well known in the state of the art, such as anionic, nonionic, cationic or amphoteric surface-active agents The make-up compositions and the sun compositions may also contain fats, organic solvents, silicones, thickeners, emollients, sun filters, anti-foams, hydrating agents, perfumes, preservatives, antioxidants, fillers, sequestering agents, treatment agents such as anionic, cationic, nonionic or amphoteric polymers or their mixtures, propellants and alkalinizing or acidifying agents.

The fats may consist of an oil or a wax or their mixture, fatty acids, fatty alcohols, white petroleum jelly, paraffin, lanolin, hydrogenated lanolin or acetylated lanolin.

The oils are chosen from animal, vegetable, mineral or synthetic oils and in particular hydrogenated palm oil, hydrogenated caster oil, liquid paraffin, paraffin oil and purcellin oil.

The waxes are chosen from animal, fossil, vegetable mineral or synthetic waxes. The following may be mentioned in particular: beeswaxes, carnauba, candellila, sugar cane and japan waxes, ozocerites, montan wax, microcristalline waxes and paraffins.

The compositions according to the invention may also contain, in addition to the lamellar particles containing melanotic pigments, as defined above, other pigments generally used in cosmetics, in particular pigments which are iridescent and/or impart iridescence, making it possible to vary the colorings which may be obtained, or to increase the protection against ultraviolet radiation. In this latter case, metal oxide pigments, such as titanium oxide, zinc oxide, cerium oxide or zirconium oxide, are used.

"Nanopigments" having an average diameter of less than 100 nm and preferably of between 5 and 50 nm are preferentially used. The nanopigments may be coated or non-coated.

The coated pigments are pigments which have undergone one or more surface treatments of a chemical, electronic, mechanochemical and/or mechanical nature with compounds as described, for example, in COSMETICS and TOILETRIES, February 1990, volume 105, pages 53–64, such as aminoacids, beeswax, fatty acids, fatty alcohols, anionic surfactants, lecithins, the sodium, potassium, zinc, iron or aluminium salts of fatty acids, metal (titanium or aluminium) alkoxides, polyethylene, silicones, proteins (collagen, elastin) alkanolamines, silicon oxides, metal oxides or sodium hexametaphosphate.

The medium used in these various cosmetic compositions is a medium which is essentially a non-solvent for the inorganic or organic particles having a lamellar structure, containing the melanotic pigment.

The term essentially non-solvent medium is used to denote a medium which dissolves less than 1% by weight of the lamellar particles.

A further subject of the invention is a process for dyeing hair, making up the skin or protecting the human epidermis against the harmful effects of UV radiation, using a powder based on organic or inorganic particles having a lamellar structure and containing melanotic pigments, as defined above, this powder being applied directly or by means of cosmetic compositions as defined above.

The following examples are intended to illustrate the invention without, however, having a limiting character.

EXAMPLE 1

5 g ($3.3 \times 10^{-2}$ mol) of 5,6-dihydroxyindole are dissolved in 100 ml of a 0.1% aqueous ammonia solution. 45 g of bismuth oxychloride, sold under the name PEARL GLO UVR 1086 by MALLINCKRODT, are added to this mixture and the suspension is stirred for 15 minutes and then brought to 80° C. 28.77 g of aqueous hydrogen peroxide containing 2.3 g ($6.7 \times 10^{-2}$ mol) of hydrogen peroxide are added in the course of 15 minutes, keeping the temperature between 80° and 85° C. When the addition is complete, the temperature is kept at 80° C. for 2 hours and the reaction mixture is then cooled to 10° C. The product is drained and washed with water. After drying, 48 g of deep brown powder are obtained.

EXAMPLE 2

5 g ($3.3 \times 10^{-2}$ mol) of 5,6-dihydroxyindole are dissolved in 100 ml of a 0.1% aqueous ammonia solution. 45 g of boron nitride, sold under the name SH P2 by KANASAKI, are added to this mixture and the suspension is stirred for 15 minutes and then brought to 80° C. 28.77 g of aqueous hydrogen peroxide containing 2.3 g ($6.7 \times 10^{-2}$ mol) of hydrogen peroxide are added in the course of 15 minutes, keeping the temperature between 80° and 85° C. When the addition is complete, the temperature is kept at 80° C. for 2 hours and the reaction mixture is then cooled to 10° C. The product is drained and washed with water. After drying, 48 g of deep brown powder are obtained.

EXAMPLE 3

7 g ($4.6 \times 10^{-2}$ mol) of 5,6-dihydroxyindole are dissolved in 140 ml of 0.1% aqueous ammonia solution. 63 g of mica, sold under the name MICA CONCORD 1000 by SCIAMA, are added to this mixture and the suspension is stirred for 15 minutes and then brought to 80° C. 24 g of aqueous hydrogen peroxide containing 3.12 g ($9.2 \times 10^{-2}$ mol) of hydrogen peroxide are added in the course of 1 hour, keeping the temperature between 80° and 85° C. When the addition is complete, the temperature is kept at 80° C. for 1 hour and the reaction mixture is then cooled to 20° C. The precipitate is drained and washed with water. After drying, 70 g of deep brown powder are obtained.

EXAMPLE 4

11.1 g of 5,6-dihydroxyindole are dissolved in 243 ml of 2% aqueous ammonia solution. 100 g of red transparent iron oxide sold under the name CAPPOXYT ROUGE 4435 B by CAPPELLE, are added to this mixture and the suspension is heated to 80° C. 28.57 g of 110 volume hydrogen peroxide, diluted in 84 g of ion-exchanged water, are added in the course of 30 minutes, keeping the temperature between 80° and 85° C. When the addition is complete, heating is continued for 2 h 30 minutes at 80°–85° C. and the reaction mixture is then cooled to 20° C. The precipitate is drained and washed with water. After drying, 108.2 g of black-brown powder are obtained.

APPLICATION EXAMPLES

EXAMPLE 1

An oil-in-water sun emulsion having the following composition is prepared:

| | |
|---|---|
| Mixture of cetylstearyl alcohol and oxyethylenated cetylstearyl alcohol containing 33 mol of ethylene oxide, sold under the name "SINNOWAX AO" by HENKEL | 7.0 g |
| Non-autoemulsifiable mixture of glyceryl monostearate and glyceryl distearate | 2.0 g |
| Cetyl alcohol | 1.5 g |
| Silicone oil | 1.5 g |
| Liquid paraffin | 15.0 g |
| Melanotic pigment prepared in accordance with Example 2 | 1.0 g |
| Glycerol | 20.0 g |
| Perfume, preservative qs | |
| Water qs | 100.0 g |

EXAMPLE 2

An oil-in-water sun emulsion having the following composition is prepared:

| | |
|---|---|
| Mixture of cetylstearyl alcohol and oxyethylenated cetylstearyl alcohol containing 33 mol of ethylene oxide, sold under the name "SINNOWAX AO" by HENKEL | 7.0 g |
| Non-autoemulsifiable mixture of glyceryl monostearate and glyceryl distearate | 2.0 g |
| Cetyl alcohol | 1.5 g |
| Silicone oil | 1.5 g |
| Liquid paraffin | 15.0 g |
| 2-ethyl-hexyl para-methoxycinnamate, sold under the name "PARSOL MCX" by GIVAUDAN | 5.0 g |
| Melanotic pigment prepared in accordance with Example 1 | 2.0 g |
| Glycerol | 20.0 g |
| Yellow iron oxide qs | |
| Red iron oxide gs | |
| Perfume, preservative qs | |
| Water qs | 100.0 g |

EXAMPLE 3

An oil-in-water sun emulsion having the following composition is prepared:

| | |
|---|---|
| Mixture of cetylstearyl alcohol and oxyethylenated cetylstearyl alcohol containing 33 mol of ethylene oxide, sold under the name "SINNOWAX AO" by HENKEL | 7.0 g |
| Non-autoemulsifiable mixture of glyceryl monostearate and glyceryl distearate | 2.0 g |
| Cetyl alcohol | 1.5 g |
| Silicone oil | 1.5 g |
| Liquid paraffin | 15.0 g |
| 2-ethyl-hexyl para-methoxycinnamate, sold under the name "PARSOL MCX" by GIVAUDAN | 5.0 g |
| Melanotic pigment prepared in accordance with Example 3 | 0.5 g |
| Glycerol | 20.0 g |
| Perfume, preservative qs | |
| Water qsp | 100.0 g |

EXAMPLE 4

A hair dyeing gel having the following composition is prepared:

| | |
|---|---|
| Melanotic pigment prepared in accordance with Example 1 | 2.0 g |
| Crosslinked polyacrylic acid (molecular weight 4,000,000) sold under the name "CARBOPOL 940" by GOODRICH | 0.7 g |
| Ethyl alcohol | 17.0 g |
| Triethanolamine qs pH = 7.5 | |
| Water qs | 100.0 g |

The composition is applied to hair which is 100% white. After uniform distribution of the product, the hair is dried at 60° C. for about 15 minutes. The hair is dyed light grey.

EXAMPLE 5

An oil-in-water sun emulsion having the following composition is prepared:

| | |
|---|---|
| Melanotic pigment prepared in accordance with Example 4 | 0.15 g |
| Titanium oxide coated with alumina and aluminium stearate, sold under the name "MICRO TiO$_2$ MT 100T" by TAYCA | 5.0 g |
| SINNOWAX AO | 7.0 g |
| Non-autoemulsifiable mixture of glycerol monostearate and glycerol distearate | 2.0 g |
| Cetyl alcohol | 1.5 g |
| Silicone oil | 1.5 g |
| Liquid paraffin | 15.0 g |
| Glycerol | 20.0 g |
| Triethanolamine qs pH = 7 | |
| Perfume, preservatives qs | |
| Purified water qsp | 100.0 g |

EXAMPLE 6

An emulsion having the following composition is prepared:

| | |
|---|---|
| Melanotic pigment prepared in | 3 g |

-continued

| | |
|---|---|
| accordance with Example 3 | |
| Yellow iron oxide | 1.77 g |
| Red iron oxide | 0.73 g |
| Titanium oxide | 3.5 g |
| Ammonium magnesium silicate | 1.0 g |
| Mixture of glycidol monostearate and distearate, stearic acid and glycerol sold under the name "GELEOL Copeaux" by GATTEFOSSE | 2.2 g |
| Capric and caprylic acid triglycerides | 15 g |
| Stearic acid | 2.2 g |
| Triethanolamine | 1.0 g |
| Sodium lauroyl sarcosinate | 0.6 g |
| Cyclic dimethyl polysiloxane | 10.0 g |
| Aluminium salt of the product of the reaction between octenylsuccinic anhydride and starch | 5 g |
| Carboxymethylcellulose | 0.16 g |
| 2-Hydroxy-4-methoxybenzophenone | 0.5 g |
| 2-Ethylhexyl dimethyl-p-aminobenzoate | 0.5 g |
| Propylene glycol | 2 g |
| Glycerol | 3 g |
| Antioxidants, preservatives qs | |
| Water qs | |

We claim:

1. A product in the form of a powder consisting of organic or inorganic particles having a lamellar structure and a size less than 50 microns, said particles containing at least one synthetic melanotic pigment formed in situ by oxidation of an indole compound, wherein said indole compound has the formula

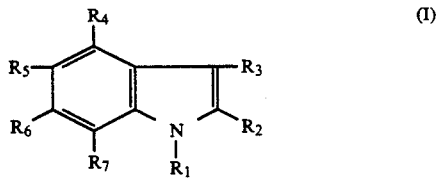

wherein
$R_1$ and $R_3$, each independently, represent hydrogen or $C_1$-$C_4$ alkyl;
$R_2$ represents hydrogen, $C_1$-$C_4$ alkyl, carboxyl or ($C_1$-$C_4$) alkoxycarbonyl;
$R_4$ and $R_7$, each independently, represent hydrogen, hydroxyl, $C_1$-$C_4$ alkyl, amino, ($C_1$-$C_4$) alkoxy, ($C_2$-$C_{14}$) acyloxy or ($C_2$-$C_4$) acylamino;
$R_5$ represents hydrogen, hydroxyl, ($C_1$-$C_4$) alkoxy, ($C_1$-$C_4$) alkyl, halogen, amino, ($C_2$-$C_4$) acyloxy, ($C_2$-$C_4$) acylamino or trimethylsilyloxy;
$R_6$ represents hydrogen, hydroxyl, ($C_1$-$C_4$) alkoxy, amino, ($C_2$-$C_4$) acyloxy, ($C_2$-$C_4$) acylamino, trimethylsilyloxy or hydroxy ($C_2$-$C_4$) alkylamino;
or $R_5$ and $R_6$, together with the carbon atoms to which they are attached, form a methylenedioxy ring optionally substituted by $C_1$-$C_4$ alkyl, $C_1$-$C_4$ alkoxy or a carbonyldioxy ring;
at least one of $R_4$ to $R_7$ represents OZ or NHR and at most one of $R_4$ to $R_7$ represents NHR; and
at most two of $R_4$ to $R_7$ represent OZ, said OZ groups being in the 5- and 6- positions when Z represents hydrogen, and at least one of $R_4$ to $R_7$ represents hydrogen and, in this case, if only one of $R_4$ to $R_7$ represents hydrogen, only one of $R_4$ to $R_7$ represents NHR or OZ, the remainder representing $C_1$-$C_4$ alkyl;
and wherein R in said NHR represents hydrogen, $C_2$-$C_4$ acyl or $C_2$-$C_4$ hydroxyalkyl and Z in said OZ represents hydrogen, $C_2$-$C_{14}$ acyl, $C_1$-$C_4$ alkyl or trimethylsilyl;
or a corresponding salt of said indole compound of formula I.

2. The product of claim 1 wherein said indole compound is selected from the group consisting of
4-hydroxyindole,
5-hydroxyindole,
6-hydroxyindole,
7-hydroxyindole,
4-hydroxy-5-methoxyindole,
4-hydroxy-5-ethoxyindole,
2-carboxy-5-hydroxyindole,
5-hydroxy-6-methoxyindole,
6-hydroxy-7-methoxyindole,
5-methoxy-6-hydroxyindole,
5,6-dihydroxyindole,
N-methyl-5,6-dihydroxyindole,
2-methyl-5,6-dihydroxyindole,
3-methyl-5,6-dihydroxyindole,
2,3-dimethyl-5,6-dihydroxyindole,
2-carboxy-5,6-dihydroxyindole,
4-hydroxy-5-methylindole,
2-carboxy-6-hydroxyindole,
6-hydroxy-N-methylindole,
2-ethoxycarbonyl-5,6-dihydroxyindole,
4-hydroxy-7-methoxy-2,3-dimethylindole,
4-hydroxy-5-ethoxy-N-methylindole,
6-hydroxy-5-methoxy-2-methylindole,
6-hydroxy-5-methoxy-2,3-dimethylindole,
6-hydroxy-2-ethoxycarbonylindole,
7-hydroxy-3-methylindole,
5-hydroxy-6-methoxy-2,3-dimethylindole,
5-hydroxy-3-methylindole,
5-acetoxy-6-hydroxyindole,
5-hydroxy-2-ethoxycarbonylindole,
6-hydroxy-2-carboxy-5-methylindole,
6-hydroxy-2-ethoxycarbonyl-5-methoxyindole,
6-N-β-hydroxyethylaminoindole,
4-aminoindole,
5-aminoindole,
6-aminoindole,
7-aminoindole,
N-methyl-6-β-hydroxyethylaminoindole,
6-amino-2,3-dimethylindole,
6-amino-2,3,4,5-tetramethylindole,
6-amino-2,3,4-trimethylindole,
6-amino-2,3,5-trimethylindole,
6-amino-2,3,6-trimethylindole,
5,6-diacetoxyindole,
5-methoxy-6-acetoxyindole and
5,6-dimethoxyindole.

3. The product of claim 1, wherein said indole compound is 5,6-dihydroxyindole or 6-hydroxyindole or a mixture thereof.

4. The product of claim 1, wherein said particles having a lamellar structure are selected from the group consisting of L-lauroyllysine, ceramic microparticles optionally covered with zirconium powder, lamellar titanium dioxide, lamellar talc, boron nitride, mica, bismuth oxychloride and red transparent iron oxide.

5. The product of claim 1 wherein said particles having a lamellar structure consist of thin plates for which the ratio between the largest dimension and the thickness is between 2 and 100.

6. The product of claim 1 wherein said particles having a lamellar structure have a size greater than 0.5 micron and less than 50 microns.

7. The product of claim 1 wherein said particles having a lamellar structure have a size greater than 0.5 micron and less than 25 microns.

8. A process for preparing the product of claim 1 comprising mixing in an aqueous medium said organic or inorganic particles having a lamellar structure with said indole compound and oxidizing said indole compound so as to form said melanotic pigment.

9. The process of claim 8 wherein the oxidation of said indole compound is effected in air at an alkaline pH.

10. The process of claim 8 wherein the oxidation of said indole compound is effected in oxygen in the presence of a metal catalyst.

11. The process of claim 8 wherein the oxidation of said indole compound is effected by the addition of an oxidizing agent selected from the group consisting of hydrogen peroxide, periodic acid or a salt thereof, a permanganate, a bichromate, sodium hypochlorite, potassium ferricyanide, ammonium persulfate, silver oxide, lead oxide, ferric chloride, sodium nitrite, a rare earth salt, ortho-benzoquinone, para-benzoquinone, ortho-benzoquinone monoimine, ortho-benzoquinone diimine, para-benzoquinone monoimine, para-benzoquinone diimine, 1,2-naphthoquinone, 1,4-naphthoquinone, 1,2-naphthoquinone monoimine, 1,2-naphthoquinone diimine, 1,4-naphthoquinone monoimine and 1,4-naphthoquinone diimine.

12. The process of claim 8 wherein the oxidation of said indole compound is effected by means of hydrogen peroxide in an ammoniacal medium.

13. The process of claim 8 wherein said aqueous medium is essentially a non-solvent for said particles having a lamellar structure and a solvent for said indole compound, said aqueous medium being water or a mixture of water and a solvent.

14. The process of claim 8 wherein said solvent is selected from the group consisting of ethyl alcohol, propyl alcohol, isopropyl alcohol, tert. butyl alcohol, an alkylene glycol, an alkylene glycol alkyl ether and methyl lactate.

15. The process of claim 8 wherein said indole compound is present in an amount ranging from 0.1 to 10 percent by weight based on the total weight of the reaction mixture and said organic or inorganic particles having a lamellar structure are present in an amount ranging from 0.05 to 35 percent by weight based on the total weight of the reaction mixture.

16. The process of claim 8 wherein said indole compound is present in an amount ranging from 0.5 to 5 percent by weight based on the total weight of the reaction mixture and said organic or inorganic particles having a lamellar structure are present in an amount ranging from 0.05 to 35 percent by weight based on the total weight of the reaction mixture.

17. A cosmetic composition comprising in a cosmetically acceptable medium a product in the form of a powder consisting of organic or inorganic particles having a lamellar structure and a size less than 50 microns, said particles containing at least one synthetic melanotic pigment formed in situ by oxidation of an indole compound, said product being present in an amount ranging from 0.1 to 35 percent by weight based on the total weight of said composition.

18. The cosmetic composition of claim 17 in the form of a lotion, a gel, a cream, a milk, a powder, a stick or a spray or foam packaged in an aerosol container.

19. The cosmetic composition of claim 17 wherein said cosmetically acceptable medium is an anhydrous or aqueous solid or pasty form for use in making up the skin, eyelashes or eyebrows.

20. The cosmetic composition of claim 17 for use in protecting human epidermis against solar UV radiation, said composition being in the form of a suspension or dispersion in a solvent or fat or being in the form of an emulsion, an ointment, a gel, a solid stick or an aerosol foam.

21. The cosmetic composition of claim 17 which also contains at least one of a fat, an organic solvent, a silicone, a thickener, an emollient, a surfactant, a sun filter, an antifoam agent, a hydrating agent, a perfume, a preservative, an antioxidant, a filler, a sequestering agent, a treatment agent, a propellant, an alkalinizing agent, an acidifying agent or another pigment.

22. The cosmetic composition of claim 17 which also includes a metal oxide nanopigment selected from the group consisting of titanium oxide, zinc oxide, cerium oxide, zirconium oxide and mixtures thereof, said nanopigment having an average diameter of less than 100 nm and being coated or non-coated.

23. The cosmetic composition of claim 17 wherein said product is present in an amount ranging from 0.5 to 20 weight percent based on the total weight of said composition.

* * * * *